United States Patent [19]
Anderson et al.

[11] Patent Number: 5,962,285
[45] Date of Patent: Oct. 5, 1999

[54] PROCESS FOR MAKING POLYCARBOXYLIC ACIDS

[75] Inventors: Kevin W. Anderson, Indian Springs; J. Douglas Wenzel, Cincinnati; Richard G. Fayter, Fairfield; Kenneth R. McVay, Hamilton, all of Ohio

[73] Assignee: Henkel Corporation, Gulph Mills, Pa.

[21] Appl. No.: 09/106,611

[22] Filed: Jun. 23, 1998

Related U.S. Application Data

[63] Continuation of application No. 08/757,555, Nov. 27, 1996, abandoned
[60] Provisional application No. 60/007,642, Nov. 28, 1995.
[51] Int. Cl.⁶ .................................. C12P 7/44; C12P 7/46; C12P 7/64
[52] U.S. Cl. ...................... 435/142; 435/134; 435/145; 435/172.1; 435/172.3; 435/252.22; 435/924
[58] Field of Search ............................ 435/142, 254.22, 435/924, 134, 145, 172.1, 172.3

[56] References Cited

U.S. PATENT DOCUMENTS

| | | | |
|---|---|---|---|
| 2,450,858 | 10/1948 | Fitzpatrick et al. | 260/406 |
| 2,813,113 | 11/1957 | Goebel et al. | 260/406 |
| 5,254,466 | 10/1993 | Picataggio et al. | 435/142 |
| 5,470,741 | 11/1995 | Oester et al. | 435/254.1 |
| 5,620,878 | 4/1997 | Picataggio et al. | 435/142 |

*Primary Examiner*—Herbert J. Lilling
*Attorney, Agent, or Firm*—Ernest G. Szoke; Wayne C. Jaeschke; John E. Drach

[57] ABSTRACT

Aliphatic polycarboxylic acids are made by a process comprising the steps of: (1) fermenting a beta-oxidation blocked *C. tropicalis* cell wherein both copies of the chromosomal POX5 gene and the chromosomal POX4A and POX4B genes are disrupted in a culture medium comprised of a nitrogen source, an organic substrate and a cosubstrate wherein the substrate is an unsaturated aliphatic compound having at least one internal carbon—carbon double bond and at least one terminal methyl group, a terminal carboxyl group and/or a terminal functional group which is oxidizable to a carboxyl group by biooxidation; (2) reacting the product of step (1) with an oxidizing agent to produce one or more polycarboxylic acids.

64 Claims, 2 Drawing Sheets

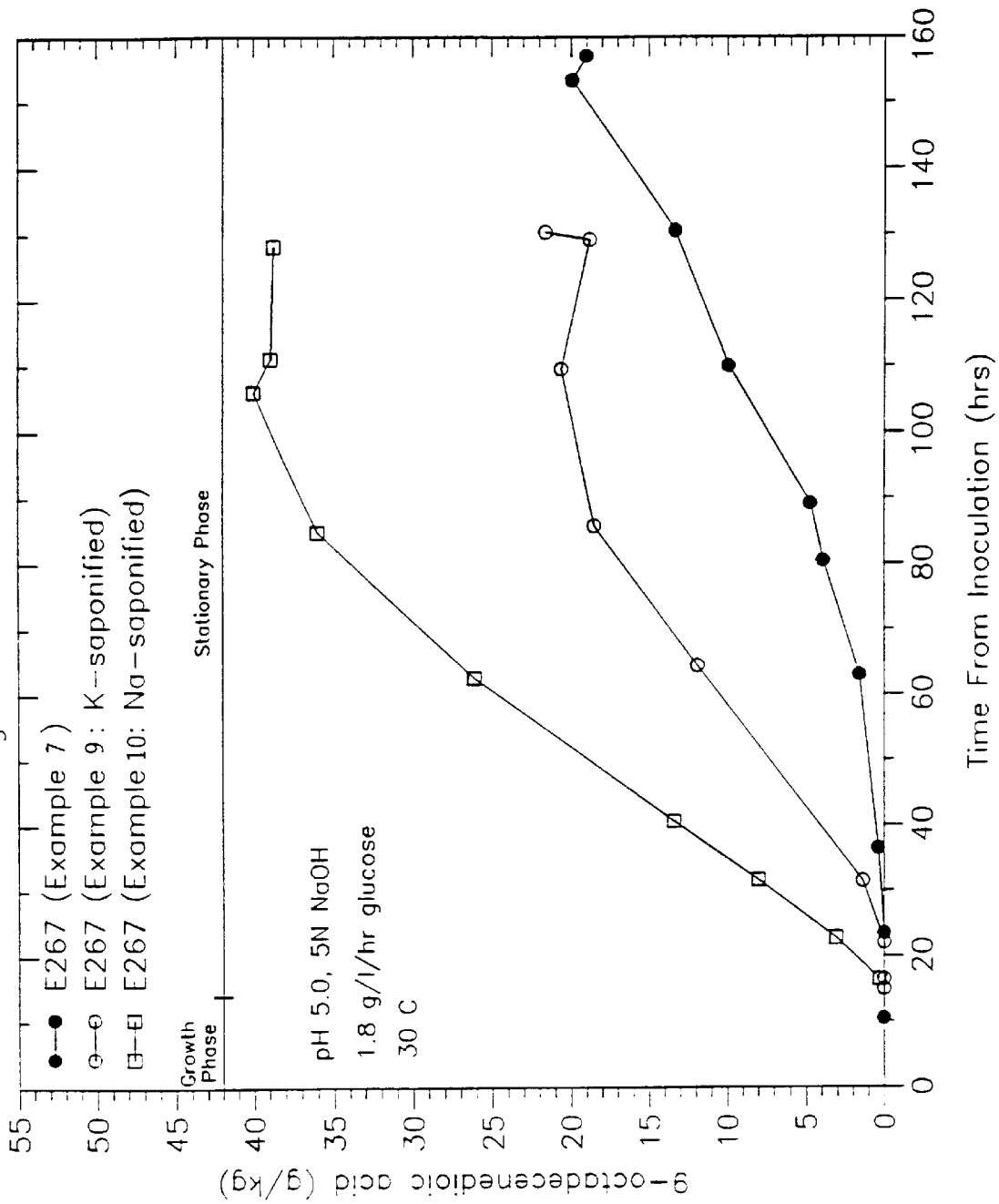

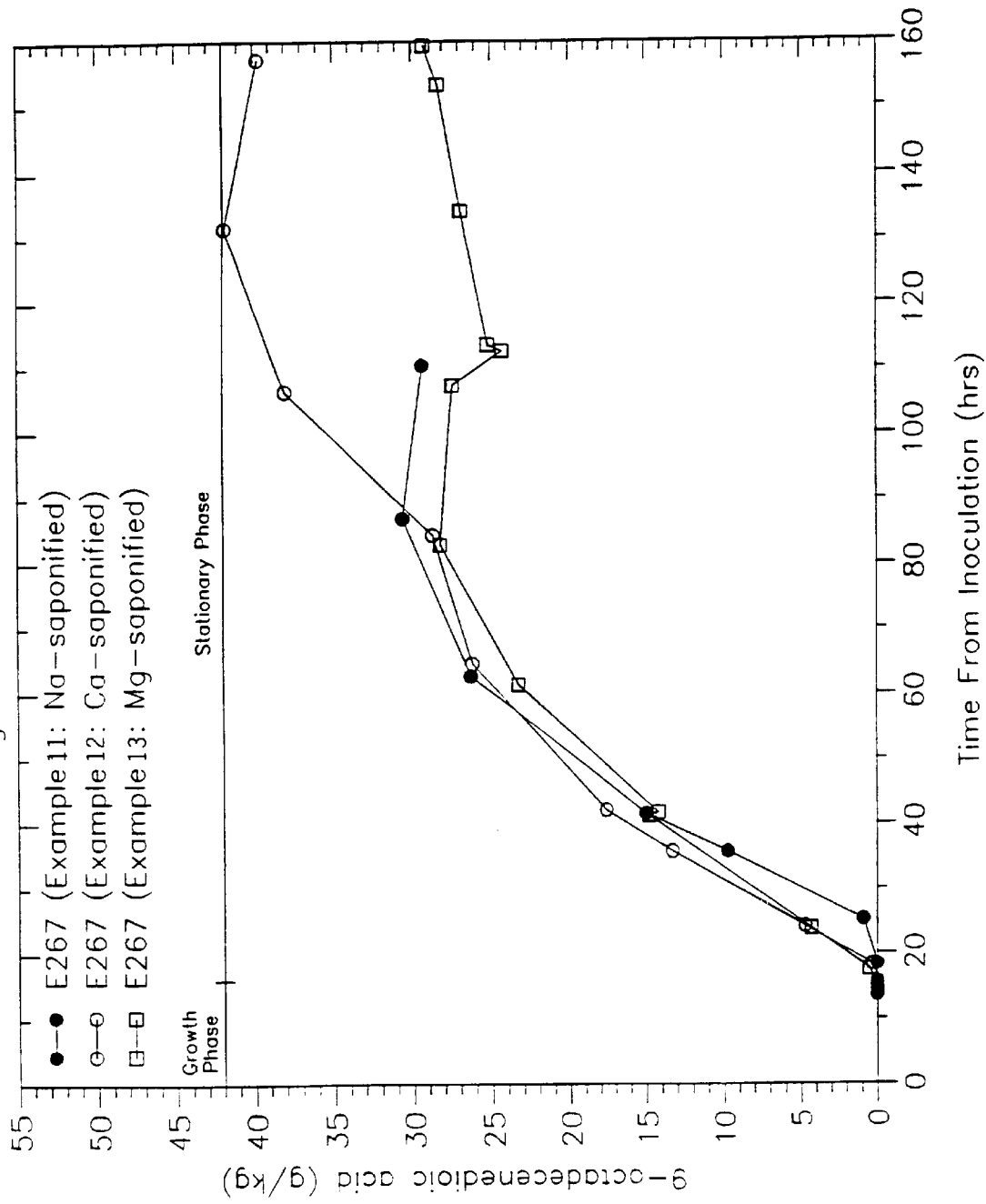

PROCESS FOR MAKING POLYCARBOXYLIC ACIDS

BENEFIT OF EARLIER FILING DATE UNDER 37 CFR 1.78(a)(4)

This application claims the benefit of earlier filed and copending provisional application Ser. No. 60/007,642, filed on Nov. 28, 1995, the entire contents of which are incorporated herein by reference and a continuation of 08/757,555 filed Nov. 27, 1996, now abandoned.

BACKGROUND OF THE INVENTION

1. Field of the Invention

This invention relates to a process for making an aliphatic polycarboxylic acid by the oxidative cleavage of one or more internal carbon—carbon double bonds in an unsaturated aliphatic compound having at least one internal carbon—carbon double bond and at least one terminal methyl group, a terminal carboxyl group and/or a terminal functional group which is oxidizable to a carboxyl group by biooxidation.

2. Description of the Related Art

Aliphatic polycarboxylic acids are versatile chemical intermediates useful as raw materials for the preparation of perfumes, polymers, adhesives and macrolid antibiotics. Aliphatic dicarboxylic acids are an especially important subclass of polycarboxylic acids which includes such commercially important acids as adipic acid, maleic acid, sebacic acid, azelaic acid, dodecanedioic acid, and dimer acid. These dicarboxylic acids are normally made from petroleum-based starting materials except azelaic acid (nonanedioic acid) and sebacic acid (decanedioic acid), which are produced from natural fats and oils in multi-million kilogram quantities.

Azelaic acid is used in the manufacture of urethane elastomers, polyester films and adhesives, plasticizers, and synthetic lubricants. Azelaic acid is the only aliphatic dicarboxylic acid having an odd number of carbon atoms that is available in large quantities.

Azelaic acid is produced commercially by ozonolysis of oleic acid as described in U.S. Pat. No. 2,813,113, the entire contents of which are incorporated herein by reference. In general, the process involves the ozonization of oleic acid to form a mixture of ozonides and subsequent oxidative work-up to form azelaic acid and pelargonic acid in a roughly equimolar amount. A major disadvantage of this process is that each mole of oleic acid produces one mole each of azelaic acid and pelargonic acid, a less desirable by-product of the process.

One way to limit or eliminate the production of pelargonic acid is to use the ω-dicarboxylic acid derivative of oleic acid, 9-octadecenedioic acid in place of oleic acid. Since the carbon—carbon double bond in 9-octadecenedioic acid is symmetrical with respect to the terminal carboxylic acid groups, the ozonolysis product of each mole of 9-octadecenedioic acid would produce 2 moles of azelaic acid and no pelargonic acid.

While several chemical routes to the synthesis of long-chain α,ω-dicarboxylic acids such as 9-octadecenedioic acid are available, such methods are complex and usually result in mixtures containing shorter chain lengths. As a result, extensive purification steps are necessary. As an alternative to chemical syntheses, long chain α,ω-dicarboxylic acids such as 9-octadecenedioic acid can be made via fermentation methods such as microbial transformation of the corresponding hydrocarbons such as alkanes or alkenes, fatty acids or esters thereof. One method for producing substantially pure α,ω-dicarboxylic acids in substantially quantitative yield is described in U.S. Pat. No. 5,254,466, the entire contents of which are incorporated herein by reference. This method comprises culturing a C. tropicalis strain wherein both copies of the chromosomal POX5 and each of the POX4A and POX4B genes are disrupted in a culture medium containing a nitrogen source, an organic substrate and a cosubstrate. Since the manufacture of polycarboxylic acids such as azelaic acid in high yield via chemical methods is difficult, it would be desirable to have a method which results in aliphatic polycarboxylic acids in high yield with a minimum of unwanted by-products.

It is therefore, an object of the present invention to provide aliphatic polycarboxylic acids in high yield with a minimum of unwanted by-products. It is also an object of the present invention to provide a specific type of polycarboxylic acids, α,ω-dicarboxylic acids, by means of a combination of biochemical and chemical methods. It is a further object of the present invention to provide azelaic acid in increased yields relative to the existing commercial process by ozonolysis of 9-octadecenedioic acid produced by fermentation of genetically modified C. tropicalis.

SUMMARY OF THE INVENTION

In its broadest aspect, the present invention relates to a process for making an aliphatic polycarboxylic acid by a process which combines biochemical and chemical process steps. The first step of the process is a biooxidation step which comprises fermenting a beta-oxidation blocked C. tropicalis cell wherein both copies of the chromosomal POX5 gene and the chromosomal POX4A and POX4B genes are disrupted in a culture medium which is comprised of a nitrogen source, an organic substrate and a cosubstrate. The organic substrate is an unsaturated aliphatic compound having at least one internal carbon—carbon double bond and at least one terminal methyl group, a terminal carboxyl group and/or a terminal functional group which is oxidizable to a carboxyl group by biooxidation. During the fermentation each terminal methyl group and/or terminal functional group which is susceptible to biooxidation is oxidized to a carboxyl group. The compound thus produced is an aliphatic compound having at least one carboxyl group and at least one carbon—carbon double bond. The second step of the process is a chemical oxidation step which involves the reaction of the product of the first step of the process with an oxidizing agent to oxidatively cleave the carbon—carbon double bonds to carboxyl groups to form one or more polycarboxylic acids.

A preferred embodiment of the present invention is a process for making azelaic acid comprising the steps of: (1) fermenting a beta-oxidation blocked C. tropicalis cell wherein both copies of the chromosomal POX5 gene and the chromosomal POX4A and POX4B genes are disrupted in a culture medium comprised of a nitrogen source, oleic acid and a cosubstrate to produce 9-octadecenedioic acid; (2) reacting 9-octadecenedioic acid with an oxidizing agent to produce azelaic acid.

BRIEF DESCRIPTION OF THE DRAWINGS

FIG. 1 is a graphical representation of the rate of 9-octadecenedioic acid production as set forth in Examples 3, 5 and 6.

FIG. 2 is a graphical representation of the rate of 9-octadecenedioic acid production as set forth in Examples 7, 8 and 9.

DESCRIPTION OF THE PREFERRED EMBODIMENTS

For purposes of the present invention, a polycarboxylic acid is any compound having two or more carboxyl groups. An internal carbon—carbon double bond is one in which each carbon atom of the double bond is bonded to at least one other carbon atom. The simplest example of a compound having an internal carbon—carbon double bond is 2-butene.

The first step of the process according to the invention comprises fermenting a beta-oxidation blocked *C. tropicalis* cell wherein both copies of the chromosomal POX5 gene and the chromosomal POX4A and POX4B genes are disrupted in a culture medium which is comprised of a nitrogen source, an organic substrate, and a cosubstrate. The organic substrate can be any unsaturated aliphatic compound having at least one internal carbon—carbon double bond and at least one terminal methyl group, a terminal carboxyl group and/or a terminal functional group which is oxidizable to a carboxyl group by biooxidation.

The beta-oxidation blocked *C. tropicalis* cell is a genetically modified *C. tropicalis* strain wherein the chromosomal POX4A, POX4B and both POX5 genes have been disrupted. The substrate flow in this strain is redirected to the omega-oxidation pathway as the result of functional inactivation of the competing β-oxidation pathway by POX gene disruption. The strain may also have one or more cytochrome P450 (P450ALK) gene and/or reductase (P450RED) genes amplified which results in an increase in the amount of rate-limiting omega-hydroxylase through P450 gene amplification and an increase in the rate of substrate flow through the ω-oxidation pathway. Preferred strains are H5343, AR40 and R24. Strain H5343 has the ATCC accession number ATCC 20962 and is described in U.S. Pat. No. 5,254,466, the entire contents of which are incorporated herein by reference. Strain AR40 is a *C. tropicalis* cell which is an amplified H5343 strain wherein all four POX4 genes and both copies of the chromosomal POX5 genes are disrupted by a URA3 selectable marker and which also contains 3 additional copies of the cytochrome P450 gene and 2 additional copies of the reductase gene, the P450RED gene. Strain AR40 has the ATCC accession number ATCC 20987. Strain R24is an amplified H5343 strain in which all four POX4 genes and both copies of the chromosomal POX5 genes are disrupted by a URA3 selectable marker and which also contains multiple copies of the reductase gene. Strains AR40 and R24 are described in copending application Ser. No. 07/975,154, filed on Nov. 12, 1992, the entire contents of which are incorporated herein by reference.

The organic substrate is any unsaturated aliphatic compound having at least one internal carbon—carbon double bond and at least one terminal methyl group, a terminal carboxyl group and/or a terminal functional group which is oxidizable to a carboxyl group by biooxidation. A terminal functional group which is a derivative of a carboxyl group may be present in the substrate molecule and may be converted to a carboxyl group by a reaction other than biooxidation. For example, if the terminal group is an ester neither the wild-type *C. tropicalis* or the genetic modifications described herein will hydrolyze the ester functionality to a carboxyl group. In such an instance, a lipase can be added during the fermentation step to liberate free fatty acids.

Examples of organic substrates which can be used in the process according to the invention include but are not limited to internal olefins such as 2-pentene, 2-hexene, 3-hexene, 9-octadecene and the like; unsaturated carboxylic acids such as 2-hexenoic acid and esters thereof, oleic acid and esters thereof including a triglyceryl esters having a relatively high oleic acid content, erucic acid and esters thereof including triglyceryl esters having a relatively high erucic acid content, ricinoleic acid and esters thereof including triglyceryl esters having a relatively high ricinoleic acid content, linoleic acid and esters thereof including triglyceryl esters having a relatively high oleic acid content; unsaturated alcohols such as 3hexen-1-ol, 9-octadecen-1-ol and the like; unsaturated aldehydes such as 3hexen-1-al, 9-octadecen-1-al and the like. In addition to the above, the organic substrate which can be used in the process according to the invention include alicyclic compounds having at least one internal carbon—carbon double bond and at least one terminal methyl group, a terminal carboxyl group and/or a terminal functional group which is oxidizable to a carboxyl group by biooxidation. Examples of such compounds include but are not limited to 3,6-dimethyl-1,4-cyclohexadiene; 3-methylcyclohexene; 3-methyl-1,4-cyclohexadiene and the like.

The fermentation step is preferably carried out in two stages. In the first stage, a culture medium is inoculated with an active culture of beta-oxidation blocked *C. tropicalis* strain where a period of rapid exponential growth occurs. In the second stage, which occurs as the cell growth of the first stage enters stationary phase, the substrate is added wherein the biooxidation described herein takes place. Since energy can no longer be produced from the substrate in beta-oxidation blocked strains, it is necessary to add a cosubstrate. The cosubstrate is a fermentable carbohydrate such as glucose, fructose, maltose, glycerol and sodium acetate. The preferred cosubstrate is glucose, preferably a liquid glucose syrup, for example, 95% dextrose-equivalent syrup, or even lower dextrose-equivalent syrups. Such materials contain small amounts of disaccharides, trisaccharides, and polysaccharides which can be hydrolyzed during the fermentation by the addition of an amylase enzyme such as α-amylase, glucoamylase and cellulase. Thus glucose can be provided in situ in a reaction simultaneous with the biooxidation. The fermentation conditions and procedures are approximately the same as those disclosed in U.S. Pat. No. 5,254,466.

The fermentation step can be modified by utilizing a triglyceride fat or oil as the source of both the organic substrate and cosubstrate. A lipase, formulated with the fermentation broth, hydrolyzes or splits the fat or oil into fatty acids and glycerine. Glycerine consumption by the organism serves to drive the splitting reaction to completion while supplying the energy necessary to convert the free fatty acids to their corresponding dibasic acids. Lipases that are oleo-specific are particularly preferred. Oleo-specific lipases exhibit a high selectivity for a triglyceride having a high oleic acid content and selectively catalyze the hydrolysis of the oleate ester groups. Examples of such oleo-specific lipases include but are not limited to the lipases produced by *Pseudomonas sp, Humicola lanuginosa, Candida rugosa, Geotrichum candidum,* and Pseudomonas (Burkholderia). A particularly preferred lipase is UNLipase from *Geotrichum candidum* ATCC No. 74170 described in U.S. Pat. No. 5,470,741, the entire contents of which are incorporated herein by reference.

The second step of the process involves the reaction of the product of the first step of the process with an oxidizing agent to oxidatively cleave the carbon—carbon double bonds to carboxyl groups to form a polycarboxylic acid. The oxidative cleavage of the carbon—carbon double bonds may be achieved with any oxidizing agent known in the art which will oxidatively cleave a carbon—carbon double bond to form two carboxyl groups. Such methods include but are not limited to reaction with ozone and subsequent oxidative work-up of the ozonides as described in U.S. Pat. No. 2,813,113, the entire contents of which are incorporated herein by reference; reaction with tungstic acid in the presence of hydrogen peroxide, preferably 60% hydrogen peroxide as described in WO 94/10122, the entire contents of which are incorporated herein by reference; reaction with chromic acid as described in U.S. Pat. No. 2,450,858, the entire contents of which are incorporated herein by reference; reaction with hypochlorite in the presence of ruthenium oxide as described in J. Am. Oil Chem. Soc., 54, 870A (1977), the entire contents of which are incorporated herein by reference; permanganate oxidation as described in, J. Am. Oil Chem. Soc., 54, 858A (1977), the entire contents of which are incorporated herein by reference; peroxyformic acid oxidation as described in U.S. Pat. No. 5,380,928, the entire contents of which are incorporated herein by reference; cobalt bromide catalyzed peroxide oxidation as described in U.S. Pat. No. 4,606,863, the entire contents of which are incorporated herein by reference; cetylpyridinium chloride catalyzed phosphotungstic acid oxidation as described in JP 2530675, the entire contents of which are incorporated herein by reference.

A preferred embodiment of the present invention is a process making one or more saturated dicarboxylic acids from a single unsaturated dicarboxylic acid substrate containing one or more carbon—carbon double bonds which are present in a carbon chain terminated by at least one of the carboxyl groups. The total number of carbon atoms in the saturated dicarboxylic acid product is equal to the number of carbon atoms in the unsaturated dicarboxylic acid. For example, 2 molecules of azelaic acid ($C_9$ acid) are made by oxidizing the carbon—carbon double bond of one molecule of 9-octadecenedioic acid ($C_{18}$ acid). In another example, one molecule each of azelaic acid ($C_9$ acid), malonic acid ($C_3$ acid), and 1,6-hexanedioic acid ($C_6$ acid) is made by oxidizing the two carbon—carbon double bonds of one molecule of linoleic acid (9,12-octadecadiendioic acid, a $C_{18}$ acid).

Another preferred embodiment of the invention is the preparation of azelaic acid by biooxidation of oleic acid to form 9-octadecenedioic acid followed by oxidation of the 9-octadecenedioic acid to azelaic acid. While any grade of oleic acid can be used as the substrate, a typical technical grade oleic acid consists of the following carboxylic acids: 0.42% $C_{12}$; 2.7% $C_{14}$; 0.86% $C_{14:1}$; 6.3% $C_{16}$; 4.6% $C_{16:1}$; 0.93% $C_{17}$; 2.8 $C_{18}$; 71.8% $C_{18:1}$; 8.3% $C_{18:2}$; 0.58% $C_{18:3}$. The oleic acid can also be a high grade oleic acid obtained from a fatty oil of a *Helianthus annuus* (sunflower seed oil) species described, for example, in U.S. Pat. No. 4,627,192, the entire contents of which are incorporated herein by reference. Such oils are very rich in oleic acid and contain at least 80% by weight of oleic.

After the 9-octadecenedioic acid has been obtained by the biooxidation method disclosed herein, it is reacted with ozone and further treated under oxidative conditions to yield azelaic acid. The mixed oxidation products are then further oxidized to azelaic acid as, for example, in the method disclosed in U.S. Pat. No. 5,420,316, the entire contents of which are incorporated herein by reference.

A number of variations of the above azelaic acid preparation are contemplated by the present invention. For example, simple esters of oleic acid such as methyl oleate, ethyl oleate, and the like can be used in place of the oleic acid in the production of 9-octadecenedioic acid as well as natural fats and oils having a relatively high oleic acid content.

The following examples are meant to illustrate but not to limit the invention.

EXAMPLE 1

Improved Method for Preparing Dicarboxylic Acids

A fermentor was charged with a semi-synthetic growth medium having the composition 75 g/l glucose (anhydrous), 6.7 g/l Yeast Nitrogen Base (Difco Laboratories), 3 g/l yeast extract, 3 g/l ammonium sulfate, 2 g/l monopotassium phosphate, 0.5 g/l sodium chloride. Components were made as concentrated solutions for autoclaving then added to the fermentor upon cooling: final pH approximately 5.2. This charge was inoculated with 5–10% of an overnight culture of *C. tropicalis* H5343 prepared in YM medium (Difco Laboratories) as described in the methods of Examples 17 and 20 of U.S. Pat. No. 5,254,466. Cells were then cultivated to about 15 g dry weight/l limited by the available nitrogen in the medium. There was a slight stoichiometric excess amount of glucose in the above charge that remained for about 4–5 hours after depletion of nitrogen sources. Air and agitation were supplied to maintain the dissolved oxygen at greater than about 40% of saturation versus air. Lower dissolved oxygen resulted in substantial in situ accumulation of partial glucose-catabolic products, primarily ethanol. The pH was maintained at about 5 by the addition of 5 N caustic soda on pH control. A technical grade oleic acid having the following composition: 0.30% $C_{12}$; 2.4% $C_{14}$; 0.60% $C_{14:1}$; 4.7% $C_{16}$; 4.6% $C_{16:1}$; 0.20% $C_{17}$; 0.80$C_{18}$; 69.9% $C_{18:1}$; 10.50% $C_{18:2}$; 0.30% C18:3 was added (100 g/l) batchwise and the glucose cosubstrate feed (1.6 g/l/hr) is started near the time the culture enters stationary phase to initiate omega oxidation. A small amount of caustic was added on pH control during the transformation to maintain the pH at 5.0. No foam was formed at any time during the transformation. After 140 hours transformation time, GLC analysis of fermentation extract indicated that 45% of the total C18:1 area counts appeared as the corresponding diacid, most of which accumulated during the last 70 hours of transformation. Other ozone feed components followed a similar pattern. Little diacid, however, accumulated during the first 60 hours of transformation.

EXAMPLE 2

Improved Method for Preparing Dicarboxylic Acids

The following method is an improvement over the method of Example 1 in that it substantially shortens the apparent induction period by partially saponifying the oleic acid to form a metal soap prior to addition to the fermentor.

Thus a fermentation conducted as in Example 1 was modified by first adding 0.0098 g KOH and 0.04 g water per gram of oleic acid to partially saponify the oleic acid. This mixture was added to the fermentation to give 50 g/l oleic acid in the fermentation broth. The saponification reaction is conveniently integrated with a thermal sterilization of the feed, if so desired, to drive the saponification reaction to completion. In contrast to the results of Example 1, dibasic acid accumulation began within 24 hours after the addition of the partially saponified fatty acids. After 115 hours transformation time, 66.7% of the total C18:1 area counts appeared as the dibasic acid. Some foaming occurred early during transformation which was easily handled by chemical or mechanical means.

EXAMPLE 3

Procedure for Making Azelaic Acid from 9-Octadecenedioic Acid

Dibasic acid from Example 2 is treated with a gas containing 5 v/o of ozone with the balance $O_2$ at a rate to supply 0.00644 mmole of $O_3$ per minute of oleic acid present in the acid mixture per minute for 2.5–3.0 hours at 23–25° C. The gas is supplied through a conventional sparger with a pore size of 147–174 μm. Afterwards, nitrogen gas is sparged into the post-reaction mixture for 15 minutes, in order to free the mixture substantially from either form of gaseous oxygen.

An amount of 23 grams of a mixture prepared as described above is placed together with 0.30 g of a Na—X Zeolite catalyst were placed in a reactor. The reactor is placed in a temperature controlled water bath and initially sparged with nitrogen while the temperature is maintained 10° below the desired reaction temperature of 60° C. The temperature controller for the water bath is then set to increase the temperature up to the desired reaction temperature. When the desired reaction temperature is reached in the water bath, the gas flow is changed from nitrogen to oxygen at a rate of 350 ml/min. The reaction is continued until the peroxide content reached about 0.25 mmole O—O/gram by the method described in Example 10 of U.S. Pat. No. 5,420,316. The product should contain azelaic acid substantially free of pelargonic acid.

EXAMPLE 4

Procedure for Making 9-Octadecenedioic Acid Utilizing a Triglyceride Fat or Oil as the Source of Both Carbohydrate and the Organic Substrate A fermentation medium is comprised of (1) growth nutrients and mineral salts, (2) a high oleic acid triglyceride, and (3) one or more lipases capable of hydrolyzing the triglyceride oil (such as a high oleic acid sunflower or canola oil), is prepared and inoculated with C. tropicalis H5343 . The growth nutrients and mineral salts are selected to support growth of C. tropicalis and maintain activity of the lipase and C. tropicalis catalysts. At least one lipase capable of effectively hydrolyzing fatty acids at all three positions is included, however 1,3-specific lipases may also be used in combination with the non-selective lipase if so desired. Supplemental amounts of carbohydrate, in addition to that stoichiometrically available from the oil splitting reaction, may also be added if so desired. The resulting fermentation, together with in situ oil splitting, should produce a product having a high 9-octadecenedioic acid content.

EXAMPLE 5

Preparation of Candida Tropicalis H5343 Fermentor Inoculum

Candida tropicalis H5343 was stored in 2 ml vials with glycerol cryoprotectant at −60 to −70° C. for use as fermentor inoculum. Cells were revived by quickly thawing a vial and pipetting 1 ml of stock into 20 ml of sterile YM Broth (Difco Laboratories). YM Broth is a complex medium suitable for cultivating a wide range of yeasts and molds. This preculture was incubated on an orbital shaker at 300 rpm 30° C. for 15 hours. Three ml of this preculture was then used to inoculate 500–550 ml of sterile YM Broth. These were subsequently incubated for 14–18 hours on an orbital shaker at 300 rpm at 30° C. for use as fermentor inoculum.

EXAMPLE 6

Growth of Candida Tropicalis H5343 for Fermentations

A semi-synthetic growth medium was selected to grow yeast cells which was similar to that previously described by Picataggio et al. (Bio/technology, 10 1992, pp 894–898). The growth medium contained (g/l unless otherwise noted):

| | |
|---|---|
| Group 1 | |
| Glucose | 70 |
| Group 2 | |
| Yeast Nitrogen Base | 6.7 |
| Group 3 | |
| Yeast Extract | 3 |
| Group 4 | |
| Ammonium Sulfate | 3 |
| Monopotassium phosphate | 2 |
| Sodium chloride | 0.5 |
| Group 5 | |
| Magnesium sulfate | 0.5 |
| Group 6 | |
| Calcium chloride | 0.1 |
| Group 7 | |
| Ferrous sulfate | 0.04 |
| Group 8 | |
| Antifoam | 2 ml |

Yeast Nitrogen Base and Yeast Extract are both products of Difco Laboratories. Antifoam was SAG 471, a product of Union Carbide. In some cases, hydrated components were used with appropriate correction for water of hydration. Components from group 4 were sterilized in the fermentor. Other components were sterilized separately and added to the fermentor after cooling. Group 7 was acidified with sulfuric acid then filter sterilized. Final pH of the mixture was about 5.2. Component concentrations were adjusted, as noted, in some fatty acid oxidation examples. The fermentor was a 20 liter Chemap fermentor equipped with a bottom drive agitator shaft on which were mounted three Rushton turbines and was typically charged with 10 liters growth medium. The fermentor was inoculated with the inoculum prepared in Example 5. The temperature was maintained at 30–35° C. and the dissolved oxygen was maintained at 30% or greater to prevent ethanol formation in the presence of excess glucose using a combination of aeration, agitation, and vessel back pressure. Maintaining a dissolved oxygen level of 30% near the end of the growth phase when the cell population becomes quite dense was difficult, and the dissolved oxygen level would drop below 30% for a short period of time before stationary phase occurred. The pH was controlled at 5.0 using either 5 N sodium hydroxide or 5 N potassium hydroxide. Cells were then cultured in exponential growth. A typical fermentation consumed about 300 ml of base during growth for pH control. Entry into stationary phase began when the culture medium became depleted in nitrogen and was readily detected by a rapid rise in dissolved oxygen and a somewhat slower rise in pH. No pH adjustments were made to neutralize natural pH increases. The final stationary phase population was 4×10E9 CFU/ml or about 38 grams dry weight per liter. A cosubstrate glucose feed (50% glucose in water) was supplied to the stationary phase culture for cell maintenance and to supply energy needs associated with the production of dicarboxylic acids.

EXAMPLE 7

Oxidation of Oleic Acid to Dicarboxylic Acids

A technical grade of oleic acid having the approximate composition 0.3% C12, 2.4% C14, 0.6% C14:1, 4.7% C16, 4.6% C16:1, 0.2% C17, 0.8% C18, 69.9% C18:1, 10.5% C18:2, 0.3% C18:3 is defined as E267. A stationary phase culture was prepared using the method of Example 2 except using glucose 75 g/l and omitting component groups 5, 6, and 7. The pH was controlled at pH 5 by automatic addition of 5 N Sodium hydroxide. The glucose feed solution was supplied at 32 g/hr and 1000 g E267 was added batchwise as the culture entered stationary phase to start the oxidation of E267 to dicarboxylic acids. The oxidation of E267 proceeded at pH 5 as shown in FIG. 1. An additional 180 ml of 5 N Sodium hydroxide and 2057 g glucose solution was consumed during the fatty acid oxidation. Surprisingly, no additional antifoam was required during the oxidation phase and no viscosity problems were seen with the fermentation broth. Gas chromatographic analysis showed that 9-octadecendioic acid accumulated to 20 g/Kg. That analysis also showed that other fatty acid components of E267 were likewise converted to their corresponding dicarboxylic acid giving a total dicarboxylic acids accumulated in the fermentation broth of 29 g/Kg. This example provides a method for preparing dicarboxylic acids at an acidic pH. The advantages over previous methods in which the oxidation is done at alkaline pH is that little expensive antifoam is needed for foam control and less base is needed to maintain pH. While base is relatively inexpensive, it can occupy a substantial volume of the fermentor, diluting the product, requiring a larger fermentor vessel to be constructed. Viscosity problems had been anticipated but were not observed during the fermentation.

EXAMPLE 8

Preparation of a Partially Saponified Fatty Acid Feed

It has been found that the production of dicarboxylic acids can be made to start much earlier in the fermentation if the fatty acids are first partially neutralized to their fatty acid soaps. In general, the extent to which a fatty acid feed to the fermentation is partially neutralized will be 5% or less to cause rapid induction of dicarboxylic acid production and rapid accumulation of dicarboxylic acids. It has also been found, however, that a partially saponified feed can also be effective in altering the rheological properties of the fermentation broth. Suitable saponification reagents include metal hydroxides, carbonates, or oxides. Also metal chlorides, sulphates, or phosphates can be used with or without a saponification catalyst. These are added to the fatty acid fermentation substrate to obtain partial neutralization. The saponification reaction is aided by heating and is conveniently integrated with a heat sterilization procedure if desired. A small amount of water can also be added both to aid the sterilization and the saponification reaction. Alternatively, fatty acid soaps can be made or purchased in which the fatty acids are completely neutralized to a metal soap. This can be blended in with a desired fermentation substrate to obtain the desired induction composition.

EXAMPLE 9

Fermentation Using Partially Potassium Saponified Oleic Acid

A stationary phase culture of *Candida tropicalis* H5343 was provided as in Example 7 except 0.01 g/l of Ferrous sulfate was included in the cultivation medium. The cosubstrate glucose solution was supplied at 36 g/hr during fatty acid oxidation and the culture maintained at pH 5 using 5 N NaOH. A partially saponified E267 substrate was prepared by adding 4.9 grams Potassium hydroxide and 20 grams water to 500 grams E267. This mixture was sterilized in a laboratory autoclave for 25 minutes to sterilize the mixture and complete the saponification reaction. This was added to the stationary phase culture to begin the oxidation. The pH increased to 5.7 but decreased back to 5.0 as the fermentation progressed. The accumulation of 9-octadecendioic acid is shown in FIG. 1. An additional 140 grams 5 N Sodium hydroxide solution was consumed to maintain pH 5 and 15 ml of antifoam was consumed for foam control. The addition of 166 grams E267 (not saponified) during the early part of the fermentation was not effective in controlling foam. The final fermentation broth again contained about 20 g/Kg 9-octadecenedioic acid or about 29 g/Kg total dicarboxylic acids.

EXAMPLE 10

Fermentation Using Oleic Acid Partially Saponified to Sodium Soaps

A stationary phase culture of *Candida tropicalis* H5343 was provided as in Example 9 except the growth medium contained 70 g/l glucose. The cosubstrate glucose solution was supplied at 36 g/hr and pH maintained at pH 5 using 5 N Sodium hydroxide. A partially saponified E267 substrate was prepared by adding 3.5 grams Sodium hydroxide and 30 grams water to 500 grams E267. This mixture was sterilized in a laboratory autoclave for 25 minutes to sterilize the mixture and complete the saponification reaction. The cooled mixture plus an additional 500 grams E267 (not saponified) was added to the stationary phase culture to begin the oxidation. The pH increased to 6.0 but decreased back to 5 as the fermentation progressed. The accumulation of 9-octadecenedioic acid is shown in FIG. 1. An additional 100 grams 5 N sodium hydroxide solution was consumed to maintain the pH at 5, but in contrast to partial saponification of the feed to potassium soap, no antifoam was required for foam control. The final fermentation broth contained 40 g/Kg 9-octadecenedioic acid or about 57 g/Kg total dicarboxylic acids. This method has the advantage of rapid induction and accumulation of dicarboxylic acids with no foaming and excellent broth rheological characteristics.

EXAMPLE 11

Comparative Fermentations Using Partially Sodium Saponified Oleic Acid

Additional fermentations using a substrate E267 partially saponified to sodium soaps revealed a time delay frequently occurred between the addition of this substrate and the onset of dicarboxylic acid production. The delay typically lasted 6–10 hours and was then followed by rapid accumulation of dicarboxylic acid in the medium. FIG. 2 shows a representative example of this delay where the fermentation ultimately produced 30 g/Kg 9-octadecendioic acid.

EXAMPLE 12

Fermentation Using Oleic Acid Partially Saponified to Calcium Soaps

A stationary phase culture of *Candida tropicalis* H5343 was provided as in Example 3 except the cultivation medium contained 70 g/l glucose and 0.2 g/l Ferrous sulfate. The cosubstrate glucose solution was supplied at 37 g/hr and the culture maintained at pH 5 to 5.5 using 5 N Noah. A partially saponified E267 substrate was prepared by adding 3.26 g Calcium hydroxide and 30 g water to 500 grams of E267. This mixture was sterilized in a laboratory autoclave for 25 minutes to complete the saponification reaction. This mixture was added to the stationary phase culture to begin the oxidation. The addition of this mixture caused the pH to increase to pH 5.7 but the pH returned to 5 as the fermentation progressed. A second charge of partially calcium saponified E267, similar to the first charge, was added to the fermentation after the first charge had been oxidized to 9-octadecendioic acid at about 65 hours fermentation time. The glucose solution feed rate was also reduced to 7 g/hr at 110 hours. The accumulation of 9-octadecendioic acid is shown in FIG. 2. An additional 190 grams of 5 N Sodium hydroxide solution was consumed for pH control. No foaming occurred during the oxidation and the broth remained fluid. The fermentation produced a maximum 42 g/Kg 9-octadecendioic acid or about 60 g/Kg total dicarboxylic acids. This method has the advantage of immediate induction and rapid accumulation of 9-octadecendioic acid with no foaming or rheologic problems.

EXAMPLE 13

Fermentation Using Oleic Acid Partially Saponified to Magnesium Soaps

A stationary phase culture of Candida tropicalis H5343 was prepared using the method of Example 2. The cosubstrate glucose solution was supplied at 36 g/hr during fatty acid oxidation and the culture maintained at pH 5 using 5 N Noah. A partially saponified E267 substrate was prepared by adding 2.56 grams Magnesium hydroxide and 30 g water to 500 grams E267. This mixture was sterilized in a laboratory autoclave to complete the saponification reaction. This was added to the stationary phase culture to begin the oxidation. The pH increased to 5.7 but decreased back to 5.0 as the fermentation progressed. A second 500 gram charge of similarly saponified feed was added at about 40 hours fermentation time. The accumulation of 9-octadecendioic acid in the fermentation broth is shown in FIG. 2. An additional 100 grams of 5 N Sodium hydroxide solution to maintain pH 5 was consumed during the oxidation. No foaming occurred and the broth remained fluid. This fermentation produced a maximum 28 g/Kg 9-octadecendioic acid or about 40 g/Kg total dicarboxylic acids.

EXAMPLE 14

Alternative Process for Making Dicarboxylic Acids

A stationary phase culture of Candida tropicalis H5343 was prepared using the method of Example 8 except Sodium chloride was omitted and 0.04 g/l Ferrous sulfate was added. The cosubstrate glucose solution was supplied at 31 g/hr to the stationary phase culture and the pH was maintained at 5.0 using 5 N Potassium hydroxide. A partially saponified E267 substrate was prepared by adding 0.65 g Calcium hydroxide and 12 g of water to 200 g E267. This mixture was sterilized for 25 mins. in a laboratory autoclave to complete the saponification reaction. This was added to the stationary phase culture to begin the oxidation. Similar pH changes were observed as in previous examples. Additional aliquots (250 to 290 grams each) of E267 (unsaponified) were added to the fermentation daily to give a final total E267 addition of 1800 grams. The pH of the broth was increased to between 5.75 and 6.0 on the second day of the fermentation. An additional 522 grams of 5 N Potassium hydroxide solution was consumed during the fermentation. No antifoam was needed. This fermentation produced a maximum 65 g/Kg 9-octadecendioic acid or about 93 g/Kg total dicarboxylic acids over 180 hours fermentation time. The fermentation broth became viscous as the fermentation progressed making agitation and oxygen transfer difficult.

EXAMPLE 15

Viscosity Control Using Presaponified Fatty Acid Substrates

A stationary phase culture of Candida tropicalis H5343 was prepared as in example 10. The cosubstrate glucose solution was supplied at 40 g/hr but was reduced to 25 g/hr at 84 hr fermentation time. The pH was maintained at pH 5 until 36 hours fermentation time when it was increased to pH 5.7–5.9 using 5 N Potassium hydroxide solution. A partially saponified E267 substrate was prepared by adding 1.3 grams Calcium hydroxide and 12 grams water to 200 g E267. This was sterilized to complete the saponification reaction then added to the stationary phase culture to start the production of dicarboxylic acids. Subsequent substrate additions, each being 250 g aliquots of E267, were partially saponified with either 2.5 g Potassium hydroxide or 1.6 g Calcium hydroxide in 15 grams water. These were added daily to the fermentation to give a final total E267 addition to the fermentation of 1200 g. An additional 526 g of Potassium hydroxide solution was consumed for pH control. The fermentation using this method produced a maximum 59.1 g/Kg 9-octadecenedioic acid or 85 g/Kg total dicarboxylic acids during a total 150 hour fermentation time. The fermentation broth produced no foaming and remained fluid using the combination of partially saponified feeds while producing a high concentration of dicarboxylic acids.

EXAMPLE 16

Method for Converting Pelargonic Acid to Azelaic Acid

A culture was prepared using the method of Example 11 except at 134 hours fermentation time, a 25 g aliquot of pelargonic acid diluted with 225 g E267 solvent was added to the fermentation without partial saponification. GLC analysis of the broth showed that nearly all the pelargonic acid was oxidized to azelaic acid. There appeared to be little further accumulation of 9-octadecedioic acid during the time pelargonic acid was being oxidized to azelaic acid.

EXAMPLE 17

Phase Separation Phenomena

A fermentation sample generated essentially using the method of Example 11 and containing 0.9 g/Kg unreacted oleic acid and 37.4 g/Kg 9-octadecenedioic acid was observed to spontaneously separate, under gravity, into two liquid phases and a dense solid phase comprised of the yeast cells at pH 6.0 and 70° C. Analysis of the clear light liquid phase showed it to contain only 0.2 g/kg oleic acid and 0.3 g/kg 9-octadecenedioic acid. The lower oily liquid phase contained 0.9 g/kg oleic acid and 92.1 g/Kg 9-octadecenedioic acid.

EXAMPLE 18

Utilization of Phase Separation Phenomena

A fermentation sample generated using the method of Example 11 was adjusted to pH 6.15 using 5 N Potassium hydroxide solution and collected in a 100 ml graduated cylinder. The whole sample contained 0.8 g/Kg unreacted oleic acid and 58.1 g/Kg 9-octadecenedioic acid. The cylinder was placed in an oven at 70° C. for several hours to observe subsequent phase separation. Ultimately the sample yielded 30 ml of the amber-colored light liquid phase, 22 ml of an amber oily phase, and 50 ml of the same oily phase but occluded with cells. To determine the effect of centrifugation on the phase separation, the same sample (40 ml) was placed in a conical centrifuge tube at pH 6.15, heated to 70° C., then processed for one minute in a clinical centrifuge. The sample yielded 20 ml of the light liquid phase, 15 ml of the oily liquid phase, and about 5 ml of cell pellet. The method of this Example gives an immediate primary separation of product from cell mass. The light liquid phase, which is low in unreacted substrate and dicarboxylic acid product, can be recycled to subsequent fermentations to reuse valuable components in this phase. The oily dense liquid phase is now enriched in dicarboxylic acids and is suitable for further downstream recovery steps. The cells are easily removed and optionally can be washed to recover any residual dense oily phase occluded in the interstitial spaces between cells.

DEPOSIT OF MICROORGANISMS

Living cultures of *C. tropicalis* R40 designated ATCC 20987 and strain *C. tropicalis* 5343 (ATCC 20962) have been deposited with American Type Culture Collection, 12301 Parklawn Drive, Rockville, Md. 20852 under the Budapest Treaty on the International Recognition of the Deposit of Microorganisms for the purposes of patent procedure.

What is claimed is:

1. A process for making an aliphatic polycarboxylic acid comprising the steps of: (1) fermenting a beta-oxidation blocked *C. tropicalis* cell wherein both copies of the chromosomal POX5 gene and the chromosomal POX4A and POX4B genes are disrupted in a culture medium comprised of a nitrogen source, an organic substrate and a cosubstrate wherein said substrate is an unsaturated aliphatic compound having at least one internal carbon—carbon double bond and at least one terminal methyl group, a terminal carboxyl group and/or a terminal functional group which is oxidizable to a carboxyl group by biooxidation; (2) reacting the product of step (1) with an oxidizing agent to produce one or more polycarboxylic acids.

2. The process of claim 1 wherein said *C. tropicalis* cell is H5343.

3. The process of claim 1 wherein one or more P450ALK genes, P450RED genes, or a combination thereof is amplified in said *C. tropicalis* cell.

4. The process of claim 2 wherein one or more P450RED genes is amplified in said *C. tropicalis* cell.

5. The process of claim 4 wherein said *C. tropicalis* cell is strain AR40 or R24.

6. The process of claim 1 wherein the oxidizing agent is selected from the group consisting of ozone; tungstic acid—hydrogen peroxide; chromic acid; hypochlorite—ruthenium oxide; permanganate; peroxyformic acid; cobalt bromide—hydrogen peroxide.

7. The process of claim 6 wherein said oxidizing agent is ozone.

8. The process of claim 1 wherein said organic substrate is oleic acid.

9. The process of claim 1 wherein said substrate is derived from a triglyceride having a high oleic acid content.

10. The process of claim 9 wherein said culture medium is further comprised of a lipase capable of effectively hydrolyzing said triglyceride into fatty acids and glycerine.

11. The process of claim 10 wherein said lipase is a oleo-specific lipase.

12. The process of claim 11 wherein said oleo-specific lipase is selected from the group consisting of the lipase from *Pseudomonas sp*, *Humicola lanuginosa*, *Candida rugosa*, *Geotrichum candidum*, Pseudomonas (Burkholderia) and UNLipase from *Geotrichum candidum* ATCC No. 74170.

13. The process of claim 12 wherein said lipase is UNLipase from *Geotrichum candidum* ATCC No. 74170.

14. A process for making azelaic acid comprising the steps of: (1) fermenting a beta-oxidation blocked *C. tropicalis* cell wherein both copies of the chromosomal POX5 gene and the chromosomal POX4A and POX4B genes are disrupted in a culture medium comprised of a nitrogen source, oleic acid and a cosubstrate to produce 9-octadecenedioic acid; (2) reacting 9-octadecenedioic acid with an oxidizing agent to produce azelaic acid.

15. The process of claim 14 wherein said *C. tropicalis* cell is H5343.

16. The process of claim 14 wherein one or more P450ALK genes, P450RED genes, or a combination thereof is amplified in said *C. tropicalis* cell.

17. The process of claim 15 wherein one or more P450RED genes is amplified in said *C. tropicalis* cell.

18. The process of claim 17 wherein said *C. tropicalis* cell is strain AR40 or R24.

19. The process of claim 14 wherein the oxidizing agent is selected from the group consisting of ozone; tungstic acid—hydrogen peroxide; chromic acid; hypochlorite—ruthenium oxide; permanganate; peroxyformic acid; cobalt bromide—hydrogen peroxide.

20. The process of claim 19 wherein said oxidizing agent is ozone.

21. The process of claim 14 wherein said oleic acid is derived from a triglyceride having a high oleic acid content.

22. A process for making a saturated dicarboxylic acid comprising the steps of: (1) fermenting a beta-oxidation blocked *C. tropicalis* call wherein both copies of the chromosomal POX5 gene and the chromosomal POX4A and POX4B genes are disrupted in a culture medium comprised of a nitrogen source, an organic substrate and a cosubstrate wherein said substrate is an unsaturated aliphatic compound having at least one internal carbon—carbon double bond and at least one terminal methyl group, a terminal carboxyl group and/or a terminal functional group which is oxidizable to a carboxyl group by biooxidation to form an unsaturated dicarboxylic acid having one or more carbon—carbon double bonds in a carbon chain terminated by at least one of the carboxyl groups of said unsaturated dicarboxylic acid; (2) reacting said unsaturated dicarboxylic acid with an oxidizing agent to produce one or more saturated dicarboxylic acids.

23. The process of claim 22 wherein said unsaturated aliphatic compound is oleic acid.

24. The process of claim 22 wherein said *C. tropicalis* cell is H5343.

25. The process of claim 22 wherein one or more P450ALK genes, P450RED genes, or a combination thereof is amplified in said *C. tropicalis* cell.

26. The process of claim 24 wherein one or more P450RED genes is amplified in said *C. tropicalis* cell.

27. The process of claim 25 wherein said *C. tropicalis* cell is strain AR40 or R24.

28. The process of claim 22 wherein the oxidizing agent is selected from the group consisting of ozone; tungstic acid—hydrogen peroxide; chromic acid; hypochlorite—ruthenium oxide; permanganate; peroxyformic acid; cobalt bromide—hydrogen peroxide.

29. The process of claim 28 wherein said oxidizing agent is ozone.

30. The process of claim 23 wherein said oleic acid is derived from a triglyceride having a high oleic acid content.

31. The process of claim 30 wherein said substrate is a triglyceride having a high oleic acid content.

32. The process of claim 22 wherein said culture medium is further comprised of a lipase capable of effectively hydrolyzing a triglyceride having a high oleic acid content into fatty acids and glycerine.

33. The process of claim 32 wherein said lipase is a oleo-specific lipase.

34. The process of claim 33 wherein said oleo-specific lipase is selected from the group consisting of the lipase from *Pseudomonas sp, Humicola lanuginosa, Candida rugosa, Geotrichum candidum,* Pseudomonas (Burkholderia) and UNLipase from *Geotrichum candidum* ATCC No. 74170.

35. The process of claim 34 wherein said lipase is UNLipase from *Geotrichum candidum* ATCC No. 74170.

36. A process for making azelaic acid comprising the steps of: (1) fermenting *C. tropicalis* H 5343 in a culture medium comprised of a nitrogen source, oleic acid and a cosubstrate to produce 9-octadecenedioic acid; (2) reacting 9-octadecenedioic acid with an oxidizing agent to produce azelaic acid.

37. The process of claim 36 wherein one or more P450ALK genes, P450RED genes, or a combination thereof is amplified.

38. The process of claim 36 wherein one or more P450RED genes is amplified.

39. The process of claim 37 wherein said *C. tropicalis* cell is strain AR40 or R24.

40. The process of claim 39 wherein said strain is AR40.

41. The process of claim 36 wherein said oxidizing agent is ozone.

42. The process of claim 1 wherein the fermentation of the beta-oxidation blocked *C. tropicalis* is carried out in the pH range of from about 5.0 to about 6.0.

43. The process of claim 1 wherein the substrate is further comprised of a saturated aliphatic compound having at least one terminal methyl group, a terminal carboxyl group and/or a terminal functional group which is oxidizable to a carboxyl group by biooxidation.

44. The process of claim 14 wherein the fermentation of the beta-oxidation blocked *C. tropicalis* is carried out in the pH range of from about 5.0 to about 6.0.

45. The process of claim 14 wherein the substrate is further comprised of a saturated aliphatic compound having at least one terminal methyl group, a terminal carboxyl group and/or a terminal functional group which is oxidizable to a carboxyl group by biooxidation.

46. The process of claim 22 wherein the fermentation of the beta-oxidation blocked *C. tropicalis* is carried out in the pH range of from about 5.0 to about 6.0.

47. The process of claim 22 wherein the substrate is further comprised of a saturated aliphatic compound having at least one terminal methyl group, a terminal carboxyl group and/or a terminal functional group which is oxidizable to a carboxyl group by biooxidation.

48. The process of claim 36 wherein the fermentation of the beta-oxidation blocked *C. tropicalis* H5343 is carried out in the pH range of from about 5.0 to about 6.0.

49. The process of claim 36 wherein the substrate is further comprised of a saturated aliphatic compound having at least one terminal methyl group, a terminal carboxyl group and/or a terminal functional group which is oxidizable to a carboxyl group by biooxidation.

50. A process for making an aliphatic polycarboxylic acid comprising the steps of: (1) fermenting a beta-oxidation blocked *C. tropicalis* cell wherein both copies of the chromosomal POX5 gene and the chromosomal POX4A and POX4B genes are disrupted in a culture medium comprised of a nitrogen source, an internal olefin and a cosubstrate; (2) reacting the product of step (1) with an oxidizing agent to produce one or more polycarboxylic acids.

51. The process of claim 50 wherein the fermentation of the beta-oxidation blocked *C. tropicalis* cell is carried out in the pH range of from about 5.0 to about 6.0.

52. The process of claim 50 wherein said *C. tropicalis* cell is H5343.

53. The process of claim 50 wherein one or more P450ALK genes, P450RED genes, or a combination thereof is amplified in said *C. tropicalis* cell.

54. The process of claim 52 wherein one or more P450RED genes is amplified in said *C. tropicalis* cell.

55. The process of claim 54 herein said *C. tropicalis* cell is strain AR40 or R24.

56. The process of claim 50 wherein the internal olefin is 9-octadecene.

57. The process of claim 50 wherein the oxidizing agent is selected from the group consisting of ozone; tungstic acid—hydrogen peroxide; chromic acid; hypochlorite—ruthenium oxide; permanganate: peroxyformic acid; cobalt bromide—hydrogen peroxide.

58. The process of claim 57 wherein said oxidizing agent is ozone.

59. The process of claim 50 wherein the culture medium is further comprised of oleic acid.

60. The process of claim 50 wherein the culture medium is further comprised of a substrate derived from a triglyceride having a high oleic acid content.

61. The process of claim 60 wherein said culture medium is further comprised of a lipase capable of effectively hydrolyzing said triglyceride into fatty acids and glycerine.

62. The process of claim 61 wherein said lipase is a oleo-specific lipase.

63. The process of claim 62 wherein said oleo-specific lipase is selected from the group consisting of the lipase from *Pseudomonas sp, Humicola lanuginosa, Candida rugosa, Geotrichum candidum,* Pseudomonas (Burkholderia) and UNLipase from *Geotrichum candidum* ATCC No. 74170.

64. The process of claim 63 wherein said lipase is UNLipase from *Geotrichum candidum* ATCC No. 74170.

\* \* \* \* \*